US007288381B2

(12) United States Patent
Flicker et al.

(10) Patent No.: US 7,288,381 B2
(45) Date of Patent: Oct. 30, 2007

(54) GROUP 2 ALLERGEN SPECIFIC IGE-FABS AND USE THEREOF

(75) Inventors: Sabine Flicker, Vienna (AT); Peter Steinberger, Vienna (AT); Dietrich Kraft, Vienna (AT); Rudolf Valenta, Theresienfeld (AT)

(73) Assignee: Phadia AB, Uppsala (SE)

( * ) Notice: Subject to any disclaimer, the term of this patent is extended or adjusted under 35 U.S.C. 154(b) by 122 days.

(21) Appl. No.: 10/027,725

(22) Filed: Dec. 21, 2001

(65) Prior Publication Data

US 2003/0082659 A1 May 1, 2003

(30) Foreign Application Priority Data

Dec. 29, 2000 (SE) .................................. 0004892

(51) Int. Cl.
*G01N 33/53* (2006.01)
*G01N 33/577* (2006.01)
*C07K 16/16* (2006.01)
*C12P 21/08* (2006.01)

(52) U.S. Cl. .................. 435/7.1; 435/810; 530/387.1; 530/387.3; 530/388.1; 530/388.5

(58) Field of Classification Search ............ 424/133.1, 424/141.1, 171.1; 435/810, 7.1; 530/387.3, 530/350, 387.1, 388.1, 388.5
See application file for complete search history.

(56) References Cited

U.S. PATENT DOCUMENTS 5,254,671 A * 10/1993 Chang ........................ 530/324
5,945,294 A * 8/1999 Frank et al. ................. 435/7.9

OTHER PUBLICATIONS

Kuby et al., 1994, Immunology, second edition, pp. 85-96.*
Ngo et al., 1994, The Protein Folding Problem and Tertiary Structure Prediction, pp. 492-495.*
Abaza et al, J of Protein Chemistry 11(5): 433-444, 1992.*
Steinberger et al, J Biol Chem 271(18): 10967-72, 1996.*
Harlow et al in Antibodies a Laboratory Manual, 1998, Cold Spring harbor laboratory publication, Cold Spring Harobr, NY, p. 8-10.*
Rudikoff et al, Proc Natl Acad Sci U S A 79(6): 1979-83, Mar. 1982.*
Freshney et al, in Culture of Animal Cells, A Manual of Basic Technique, Alan R Liss, Inc, 150 Fifth Ave, New York, NY 10011, 1983.*
Denepourx et al, FEBS Letters 465: 39-46, 2000.*
Ansari et al, *Biochemistry*, 28:8665-8670 (1989).
Ansari et al, *The Journal of Biological Chemistry*, 264(19):11181-11185 (1989).
Sidoli et al, *The Journal of Biological Chemistry*, 268(29):21819-21825 (1993).
Dolecek et al, *FEBS Letters 13344*, 35(3):299-304 (1993).
Roberts et al, *Allergy*, 48:615-623 (1993).
DeMarino et al, *Structure*, 7(8):943-952 (1999).
Noon et al, *The Lancet*, 1572-1573 (Jun. 10, 1911).
Bousquet et al, *J. Allergy Clin. Immunol.*, 102(4):558-562 (1998).
Durham et al, *J. Allergy Clin. Immunol.*, 102(2):157-164 (1998).
Cooke et al, *Immunity and Sensitization in Allergy*, 733-750 (1935).
Loveless, *Two Antibodies Related to Same Pollen-Antigen*, 25-50.
Huse et al, *Science*, 246:1275-1281 (1989).
Steinberger, *The Journal of Biological Chemistry*, 271(18):10967-10972 (1996).
Niederberger et al, *J. Allergy Clin. Immunol.*, 101(2):258-264 (1998).
Barbas et al, *Proc. Natl. Acad. Sci. USA*, 88:7978-2982 (1991).
Sanger et al, *Proc. Natl. Acad. Sci. USA*, 74(12):5463-5467 (1977).
Bradford, *Analytical Biochemistry*, 72:248-254 (1976).
Fling et al, *Analytical Biochemistry*, 155:83-88 (1986).
Towbin et al, *Proc. Natl. Acad. Sci. USA*, 76(9):4350-4354 (1979).
Fals et al, *J. Clin. Invest.*, 98(7):1659-1666 (1996).
Williams et al, *Immunology*, 98:123-136 (1999).
Siegel et al, *Journal of Immunological Methods*, 206:73-85 (1997).
Ermel et al, *Arthritis and Rheumatism*, 36(3):380-388 (1993).
Martin et al, *Autoimmunity*, 15:163-170 (1993).
Tomlinson et al, *J. Mol. Biol.*, 227:776-798 (1992).
Ravetch et al, *Cell*, 27:583-591 (1981).
Mattila et al, *Eur. J. Immunol.*, 25:2578-2582 (1995).
Cox et al,, *Eur. J. Immunol.*, 24:827-836 (1994).
Hieter et al, *The Journal of Biological Chemistry*, 257(3):1516-1522 (1982).
Flicker et al, *Allergy, Copenhagen*, 53, Suppl. 43, p. 113 (1998).
Flicker et al, *The Journal of Immunology*, 3849-3859 (2000).
Segal et al, *Proc. Natl. Acad. Sci. USA*, 74(7):2993-2997 (1977).

* cited by examiner

*Primary Examiner*—Christina Chan
*Assistant Examiner*—Phuong Huynh
(74) *Attorney, Agent, or Firm*—Dinsmore & Shohl LLP

(57) ABSTRACT

The present invention relates to group 2 allergen specific IgE-Fabs and whole Ig molecules as well as use thereof. More precisely, the present invention relates to grass pollen specific IgE-Fabs (Phl p2) and reagents, kits and vaccines comprising these. The invention also relates to use of group 2 specific IgE-Fabs and whole Ig for, inter alia, diagnosis, therapy and prevention of type I allergy.

19 Claims, 7 Drawing Sheets

```
              FR1
94  ACT CAG TCT CCA TCC TCC CTG TCT GTG GGA GAC AGA GTC ACC ATC AGT TGC
X93627  --C --- --- --- --- --- --- --- --A --- --- --- --- --- --- --- ---

CDR1                              FR2
94  CGG GCA AGT CAG AGA ATT AAC ACC TAT TTA AAT TGG TAT CAG CAT AAA CCA GGG
X93627  --- --- --- --- --C --- -G- --- --- --- --- --- --- --- --G --- --- ---

FR2                          CDR2                       FR3
94  AAA GCC CCT AAG CTC CTG ATC TAT GCT GCA TCC AGT TTG CAA AGT GGG GTC
X93627  --- --- --- --- --- --- --- --- --- --- --- --- --- --- --- --- ---

FR3
94  CCA TCA AGG TTC AGT GGC AGT GGA TAT GGG ACA GAC TTC ACT CTC ACC ATC AGC AGT
X93627  --- --- --- --- --- --- --- --- --C --- --- --- --E --- --- --- --- --- ---

CDR3
94  CTG CAG CCT GAA GAT TTT GCA AGT TAC TGT CAA GAG AGT CTC AGT GCC TCG
X93627  --- --A --- --- --- --- --- --C --- --- --- C-- --- TA- --- A-- --- CT-

CDR3        FR4
94  TAC ACT     TTT GGC CAG GGG ACC AAG GTG GAG ATC AAA CGA
J00242  --- ---     --- --- --- --- --- --- C-- --- --- --- ---
```

IgE-Fab αPhl p 2 pComb3H

```
                         SEQUENCE LISTING

<160> NUMBER OF SEQ ID NOS: 12

<210> SEQ ID NO 1
<211> LENGTH: 342
<212> TYPE: DNA
<213> ORGANISM: Homo sapiens

<400> SEQUENCE: 1
ctcgagtctg gcccaggact ggtgaagcct gcacagaccc tgtccctcag ctgcgctgtc     60
tctggcggct ccatccgcag tggtggttac tactggagtt ggatccgcca acacccaggg   120
aagggcctgg agtggattgg gtacatctat cacagtggga acacctacaa caacccgtcc   180
ctcaagagtc gaattgccat gtcggtagac acgtctgaga caagttctc cctgaggctg   240 aactctgtga ctgccgcgga cacggccgtg tattactgtg cgaggttaga tggctacact   300
ttggacatct ggggccaggg aaccctggtc accgtctcct ca                      342

<210> SEQ ID NO 2
<211> LENGTH: 342
<212> TYPE: DNA
<213> ORGANISM: Homo sapiens

<400> SEQUENCE: 2
ctcgagtctg gcccaggact ggtgaagcct tcacagaccc tgtccctcac ctgcactgtc     60
tctggtggct ccatccgcag tggtggttat tattggagtt gggtccgcca gcctccaggg   120
aagggcctgg agtggatcgg caacatctat cacagtggca acacctacaa caacccgtcc   180
```

```
ctcaagagtc gaattaccat gtcagtagac acgtctaaga accacttctc cctgagactg      240
acctctgtga ctgccgcgga cacggccgtc tattactgtg cgcggtcaga tgggtatact      300
ttggacaact ggggccaggg aaccctggtc accgtctcct ca                         342
```

<210> SEQ ID NO 3
<211> LENGTH: 342
<212> TYPE: DNA
<213> ORGANISM: Homo sapiens

<400> SEQUENCE: 3

```
ctcgagtctg gcccaggact ggtgaagcct tcacagaccc tgtccctcac ctgcactgtc       60
tctggtggct ccatccgcag tggtggttat tactggagtt ggatccgcca gcgtccaggg      120
aagggcctgg agtggatcgg gtacatctat cacagtggca acacctacaa caacccgtcc      180
ctcaagagtc gagttaccat gtcagtagac acgtctaaga accacttctc cctgaggctg      240
agctctgtga ctgccgcgga cacggccgtg tattactgtg cgaggtcaga tgggtacact      300
ttggacaact ggggccaggg aaccctggtc accgtctcct ca                         342
```

<210> SEQ ID NO 4
<211> LENGTH: 318
<212> TYPE: DNA
<213> ORGANISM: Homo sapiens

<400> SEQUENCE: 4

```
gagctcactc agtctccatc ctccctgtct gcatctgtgg gagacagagt caccatcagt       60
tgccgggcaa gtcagagaat aacacctat ttaaattggt atcagcataa accagggaaa      120
gcccctaagc tcctgatcta tgctgcatcc agtttgcaaa gtggggtccc atcaaggttc      180
agtggcagtg gatatgggac agacttcact ctcaccatca gcagtctgca gcctgaagat      240
tttgcaagtt actactgtca agagagtctc agtgcctcgt cacttttgg ccaggggacc      300 aaggtggaga tcaaacga                                                    318
```

<210> SEQ ID NO 5
<211> LENGTH: 318
<212> TYPE: DNA
<213> ORGANISM: Homo sapiens

<400> SEQUENCE: 5

```
gagctcaccc agtctccatc ctccctgtct gcctctgtag gagacagagt caccatcact       60
tgccgggcac gtcagagtat tagcacctat ttaaattggt atcagcagaa accggggaag      120
gcccctaagc tcctgatctg tagtgcatcc aatttgcaaa gtggggtccc atccaggttc      180
agtggcagtg gatctgggac agagttcact ctcaccatca gcaatctgca acctgaagac      240
tttgcaagtt actactgtca acagagttac actaccttat ataccttcgg ccctgggacc      300
aaactggaga tcaaacga                                                    318
```

<210> SEQ ID NO 6
<211> LENGTH: 318
<212> TYPE: DNA
<213> ORGANISM: Homo sapiens

<400> SEQUENCE: 6

```
gagctcacgc agtctccatc ttccgtgtct gcatctgtag gagacagagt caccataact       60
tgtcgggcga gtcagggtat tagcagttgg ttagcctggt atcagcagaa accagggaaa      120
gcccctaaac tcctgatcta ttctgcatcc agtttgcaaa gtggggtccc gtcaaggttc      180
```

```
agcggcagtg gatctgggac agatttcagt ctcaccatca gcagcctgca gcctgaagat    240
tctgcaactt actattgtca acaggctaac agtttcccgt acactttggg ccagggacc    300 aaggtggaaa tcaaacga                                                   318
```

<210> SEQ ID NO 7
<211> LENGTH: 114
<212> TYPE: PRT
<213> ORGANISM: Homo sapiens

<400> SEQUENCE: 7

```
Leu Glu Ser Gly Pro Gly Leu Val Lys Pro Ala Gln Thr Leu Ser Leu
1               5                   10                  15

Ser Cys Ala Val Ser Gly Gly Ser Ile Arg Ser Gly Gly Tyr Tyr Trp
            20                  25                  30

Ser Trp Ile Arg Gln His Pro Gly Lys Gly Leu Glu Trp Ile Gly Tyr
        35                  40                  45

Ile Tyr His Ser Gly Asn Thr Tyr Tyr Asn Pro Ser Leu Lys Ser Arg
    50                  55                  60

Ile Ala Met Ser Val Asp Thr Ser Glu Asn Lys Phe Ser Leu Arg Leu
65                  70                  75                  80

Asn Ser Val Thr Ala Ala Asp Thr Ala Val Tyr Tyr Cys Ala Arg Leu
                85                  90                  95

Asp Gly Tyr Thr Leu Asp Ile Trp Gly Gln Gly Thr Leu Val Thr Val
            100                 105                 110

Ser Ser
```

<210> SEQ ID NO 8
<211> LENGTH: 114
<212> TYPE: PRT
<213> ORGANISM: Homo sapiens

<400> SEQUENCE: 8

```
Leu Glu Ser Gly Pro Gly Leu Val Lys Pro Ser Gln Thr Leu Ser Leu
1               5                   10                  15

Thr Cys Thr Val Ser Gly Gly Ser Ile Arg Ser Gly Gly Tyr Tyr Trp
            20                  25                  30

Ser Trp Val Arg Gln Pro Pro Gly Lys Gly Leu Glu Trp Ile Gly Asn
        35                  40                  45

Ile Tyr His Ser Gly Asn Thr Tyr Tyr Asn Pro Ser Leu Lys Ser Arg
    50                  55                  60

Ile Thr Met Ser Val Asp Thr Ser Lys Asn His Phe Ser Leu Arg Leu
65                  70                  75                  80

Thr Ser Val Thr Ala Ala Asp Thr Ala Val Tyr Tyr Cys Ala Arg Ser
                85                  90                  95

Asp Gly Tyr Thr Leu Asp Asn Trp Gly Gln Gly Thr Leu Val Thr Val
            100                 105                 110

Ser Ser
```

<210> SEQ ID NO 9
<211> LENGTH: 114
<212> TYPE: PRT
<213> ORGANISM: Homo sapiens

<400> SEQUENCE: 9

```
Leu Glu Ser Gly Pro Gly Leu Val Lys Pro Ser Gln Thr Leu Ser Leu
1               5                   10                  15
```

```
Thr Cys Thr Val Ser Gly Gly Ser Ile Arg Ser Gly Gly Tyr Tyr Trp
            20                  25                  30

Ser Trp Ile Arg Gln Pro Pro Gly Lys Gly Leu Glu Trp Ile Gly Tyr
        35                  40                  45

Ile Tyr His Ser Gly Asn Thr Tyr Tyr Asn Pro Ser Leu Lys Ser Arg
    50                  55                  60

Val Thr Met Ser Val Asp Thr Ser Lys Asn His Phe Ser Leu Arg Leu
65                  70                  75                  80

Ser Ser Val Thr Ala Ala Asp Thr Ala Val Tyr Tyr Cys Ala Arg Ser
                85                  90                  95

Asp Gly Tyr Thr Leu Asp Asn Trp Gly Gln Gly Thr Leu Val Thr Val
            100                 105                 110

Ser Ser
```

<210> SEQ ID NO 10
<211> LENGTH: 106
<212> TYPE: PRT
<213> ORGANISM: Homo sapiens

<400> SEQUENCE: 10

```
Glu Leu Thr Gln Ser Pro Ser Ser Leu Ser Ala Ser Val Gly Asp Arg
1               5                   10                  15

Val Thr Ile Ser Cys Arg Ala Ser Gln Arg Ile Asn Thr Tyr Leu Asn
            20                  25                  30

Trp Tyr Gln His Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Tyr Gly Thr Asp Phe Thr Leu Thr Ile Ser Ser Leu Gln Phe Glu Asp
65                  70                  75                  80

Phe Ala Ser Tyr Tyr Cys Gln Glu Ser Leu Ser Ala Ser Tyr Thr Phe
                85                  90                  95

Gly Gln Gly Thr Lys Val Glu Ile Lys Arg
            100                 105
```

<210> SEQ ID NO 11
<211> LENGTH: 106
<212> TYPE: PRT
<213> ORGANISM: Homo sapiens

<400> SEQUENCE: 11

```
Glu Leu Thr Gln Ser Pro Ser Ser Leu Ser Ala Ser Val Gly Asp Arg
1               5                   10                  15

Val Thr Ile Thr Cys Arg Ala Arg Gln Ser Ile Ser Thr Tyr Leu Asn
            20                  25                  30

Trp Tyr Gln Gln Lys Pro Gly Lys Ala Pro Lys Leu Leu Ile Trp Ser
        35                  40                  45

Ala Ser Asn Leu Gln Ser Gly Val Pro Ser Arg Phe Ser Gly Ser Gly
    50                  55                  60

Ser Gly Thr Glu Phe Thr Leu Thr Ile Ser Asn Leu Gln Phe Glu Asp
65                  70                  75                  80

Phe Ala Ser Tyr Tyr Cys Gln Gln Ser Tyr Thr Thr Leu Tyr Thr Phe
                85                  90                  95

Gly Ser Gly Thr Lys Leu Glu Ile Lys Arg
            100                 105
```

```
<210> SEQ ID NO 12
<211> LENGTH: 106
<212> TYPE: PRT
<213> ORGANISM: Homo sapiens

<400> SEQUENCE: 12

Glu Leu Thr Gln Ser Pro Ser Val Ser Ala Ser Val Gly Asp Arg
1               5                   10                  15

Val Thr Ile Thr Cys Arg Ala Ser Gln Gly Ile Ser Ser Trp Leu Ala
                20                  25                  30

Trp Tyr Gln His Gln Pro Gly Lys Ala Pro Lys Leu Leu Ile Tyr Ser
            35                  40                  45

Ala Ser Ser Leu Gln Ser Gly Val Pro Ser Arg Phe Ser Gly Ser Gly
        50                  55                  60

Tyr Gly Thr Asp Phe Ser Leu Thr Ile Ser Ser Leu Gln Phe Glu Asp
65                  70                  75                  80

Ser Ala Thr Tyr Tyr Cys Gln Gln Ala Asn Ser Phe Pro Tyr Thr Phe
                85                  90                  95

Gly Gln Gly Thr Lys Val Glu Ile Lys Arg
                100                 105
```

GROUP 2 ALLERGEN SPECIFIC IGE-FABS AND USE THEREOF

FIELD OF THE INVENTION

The present invention relates to group 2 allergen specific IgE-Fabs and use thereof. More precisely, the present invention relates to grass pollen specific IgE-Fabs (Phl p2) and reagents, kits and vaccines comprising these The invention also relates to use of group 2 specific IgE-Fabs for, inter alia, diagnosis, therapy and prevention of type I allergy

BACKGROUND OF THE INVENTION

Almost 500 million individuals suffer from Type I allergy, a genetically determined hypersensitivity disease which is based on the formation of IgE antibodies against per se harmless antigens (i.e., allergens) (1). The symptoms of Type allergy (allergic rhinitis, conjunctivitis and allergic asthma) are mainly caused by the crosslinking of effector-cell bound specific IgE antibodies and the consecutive release of biological mediators (e.g, histamine, leukotriens) (2).

Grasses and corn are distributed worldwide, produce large amounts of pollen which become easily airborn and therefore belong to the most important allergen sources. More than 40% of allergic patients are sensitized against grass pollen allergens of which group 2 allergens represent one of the most frequently recognized allergens (3, 4). Group 2 allergens occur in pollen of many grass species as highly homologous proteins with a molecular weight of approximately 10-11 kDa. Approximately 70% of grass pollen allergic people are cross-sensitized to group 2 allergens which is due to sequence, structural, and immunological similarities of group 2 allergens from different grass and corn species (5-7). Recombinant Phl p 2 from timothy grass has been produced as immunologically active recombinant protein which equals the properties of the natural allergen (6). Moreover the three dimensional structure of rPhl p 2 has been recently determined by NMR analysis and was found to resemble structural features of an immunoglobulin-like domain (8).

Specific therapy of Type I allergy can be achieved in principle by active and passive vaccination. Active vaccination is achieved by specific immunotherapy in order to induce unresponsiveness towards allergens. Although successfully practised since 1911, the immunologically mechanisms of specific immunotherapy are not completely understood (9, 10). Induction of blocking antibodies of the IgG class which interfere with the IgE allergen interaction, modulation of T cell and effector cell responses and generation of tolerance are discussed as possible mechanisms (11). In contrast to active vaccination, passive vaccination is based on the transfer of protective immunoglobulins and represents a routine treatment for many infectious diseases (e.g., hepatitis). The therapeutical efficacy of "passive vaccination" for the treatment of Type I allergy has been demonstrated by classical experiments more than 60 years ago. In 1935 Cooke and collegues reported cure of a hayfever patient by transfer of blood from a patient who had been successfully treated by specific immunotherapy (12). A few years later Loveless showed that the protective effects reported by Cooke are due to blocking antibodies (13) There are several arguments why blocking antibodies may be useful for passive therapy of Type I allergy. First, IgE is the least abundant class of immunoglobulins which could be easily competed. Second, allergic reactions occur in target organs (nose, eyes, lung, skin) where it would be easy to apply blocking antibodies or other competitors of the IgE-allergen interaction avoiding the need of systemic application. The application of the "passive vaccination concept" for treatment of Type I allergy requires however progress in the field of allergen characterization and antibody technology.

SUMMARY OF THE INVENTION

The present invention provides human IgE-Fabs suitable for diagnosis and immunotherapy of type I allergy.

In a first aspect, the invention provides group 2 allergen (i.e. pollen allergen from different grass and corn species) specific human IgE Fabs having the amino acid sequences as shown in SEQ ID NO: 7-SEQ ID NO: 12 or essentially homologous variants thereof. In a second aspect, the invention provides group 2 allergen specific human IgE Fabs encoded by the nucleic acid sequences as shown in SEQ ID NO: 1-SEQ ID NO: 6 or essentially homologous variants thereof. For example, variants caused by the degeneracy of the genetic code. The present invention also provides group 2 allergen specific human IgG comprising the variable regions of the above IgE Fabs. Preferably, the whole Ig molecules of the invention are of IgG1 subtype. The present inventors have grafted variable regions of the IgE Fabs of the invention onto human IgG1 using a known vector system. Surprisingly, these complete IgG1 antibodies strongly suppress Phi p2-induced degranulation of patients basophils which indicates their potential for clinical application.

The IgE-Fabs and/or whole Ig according to the invention are directed against Phl p 2, i.e. pollen from timothy grass but cross-react with several other pollen allergens. The IgE-Fabs and/or whole Ig according to the invention may be recombinantly produced.

In a third aspect, the invention relates to a diagnostic reagent comprising the IgE-Fabs and/or whole Ig according to the invention. Alternatively the reagent comprises the corresponding complete antibodies, and/or modified versions of said Fabs and/or antibodies.

In a fourth aspect, the invention relates to a diagnostic kit comprising the reagent mentioned above. The kit may be any conventional kit for performing an immunoassay.

In a fifth aspect, the invention relates to a vaccine against type I allergy, comprising the IgE-Fabs and/or whole Ig according to the invention.

A preferred use of Phl p 2-specific IgE-Fabs and/or whole Ig and the vaccine according to the invention is for passive immunotherapy of type I allergy. The use may be in preventive or therapeutic purpose.

Another use of Phl p 2-specific IgE-Fabs and/or whole Ig according to the invention is for diagnosing of type I allergy.

A further use of Phl p 2-specific IgE-Fabs and/or whole Ig according to the invention is for environmental allergen detection.

Yet a further use of f Phl p 2-specific IgE-Fabs and/or whole Ig according to the invention is for standardization of allergen extracts.

In order to obtain specific competitors of human origin which interfere with the IgE allergen interaction the inventors used the combinatorial library technique (14) An IgE combinatorial library was constructed from lymphocytes of a grass pollen allergic patient (15). The present invention provides human IgE Fabs with specificity for group 2 grass pollen allergens. The human IgE Fabs lack their constant region and therefore cannot activate effector cells to release biologically active mediators. The binding site of the IgE Fabs on group 2 allergens were mapped using recombinant fragments of the major timothy grass pollen allergen Phl p 2 and the crossreactivity of the IgE Fabs with group 2 allergens from different grass and corn species was investigated. Furthermore the Phl p 2-specific IgE Fabs are useful for the identification of group 2 allergen-containing pollen by particle blotting. By ELISA competition experiments, the ability of the IgE Fabs to block binding of grass pollen allergic patients IgE antibodies to Phl p 2 was analyzed. The usefulness of the recombinant group 2-specific IgE Fabs for the detection of environmental allergen loads, the standardization of diagnostic and therapeutic allergen extracts and for passive therapy of grass pollen allergy are discussed.

DETAILED DESCRIPTION OF THE INVENTION

MATERIALS AND METHODS

Biological Materials, Patients Sera, Antibodies

Pollen from sweet vernal grass, oat, Bermuda grass, rye grass, common reed, Kentucky Bluegrass, rye, wheat and maize were purchased from Allergon (Välinge, Sweden). Sera were collected from grass pollen-allergic patients who were characterized by case history, skin prick testing, RAST, and by testing with recombinant grass pollen allergens as described (16) Sera from non allergic individuals were included as negative controls $^{125}$I-labeled anti-human IgE antibodies (RAST) were obtained from Pharmacia (Pharmacia & Upjohn Diagnostics AB, Uppsala, Sweden).

E. coli strain XL1-Blue was obtained from Stratagene (La Jolla, Calif.), and plasmid pComb3H representing a modification of plasmid pComb3 (17) was kindly provided by Carlos F. Barbas, Scripps (LaJolla, Calif.). Alkaline phosphatase-coupled goat anti-human Fab and goat anti-mouse Fab antisera were purchased from Pierce (Rockford, Ill.).

Sequence Analysis of the cDNAs Coding for IgE Fds and Light Chains

Three phage clones expressing antibody fragments with specificity for Phl p 2 were isolated by panning to rPhl p 2 as described (15). All three clones were checked for the production of Phl p 2-specific Fabs by ELISA and for the correct insertion of cDNAs coding for the heavy chain fragments and the light chains by restriction analysis before sequencing. Plasmid DNA was prepared from recombinant E. coli XL-1 Blue using Qiagen tips (Hilden, Germany). Both DNA strands were sequenced using $^{35}$S-dCTP (DuPont NEN, Stevenage, UK) and a T7 polymerase sequencing kit (Pharmacia) by primer walking (18). Sequencing primers were obtained from MWG (MWG AG- Biotech, Ebersberg, Germany). The Phl p 2-specific DNA sequences of the heavy chain fragments and the light chains were compared with the germline sequences deposited in the V Base Sequence Directors (Tomlinson et al., MRC Centre for Protein Engineering, Cambridge, UK).

Expression of rPhl p 2-specific Fabs in E. coli

E. coli XL1-Blue cells containing the rPhl p 2-specific Fab expressing pComb3H plasmids were grown in SB medium containing 50 µg/ml ampicillin at 37° C. up to O D. 600 nm$^{0\ 6-1}$. After induction with 1.5 mM IPTG, cells were incubated for four hours at 32° C. Induced E. coli were harvested by centrifugation at 5000 rpm for 20 min at 4° C. and supernatants were stored at −20° C. for ELISA analysis. Cells were resuspended in PBS containing 1 mM PMSF, homogenized with an ultraturrax (Ika, Stauffen, Germany) and centrifuged at 18,000 rpm for 20 min at 4° C. (extract). The extracts were tested in ELISA assays for their binding capacity to rPhl p 2 as described (15).

Expression of Recombinant Fragments of the Phl p 2 Allergen for Mapping of the Binding Sites of the Human IgE Fabs Lambda gt11 phage clones expressing β-galactosidase fused complete Phl p 2 and Phl p 2 fragments were generated as described (8). E. coli Y1090 were plated as confluent lawn onto LB plates containing 100 mg/l ampicillin (19). Two µl aliquots of phage lysates containing >10$^6$ plaque-forming units of each phage clone were dotted onto the E. coli lawn in defined order and plates were incubated at 43° C. until plaques became visible. The synthesis of recombinant protein was induced by overlay with 10 mM IPTG-soaked nitrocellulose filters (Schleicher& Schuell, Dassel, Germany) for additional 4 hours The clones which reacted with the IgE Fabs were identified by immunoscreening. For this purpose filters were washed twice for 5 min and once for 30 min with TBST containing 0.5% w/v BSA at roomtemperature and then probed overnight with E. coli extracts containing anti-Phl p 2 Fab and, for control purposes, with extracts from E. coli transformed with the empty pComb 3H plasmid at 4° C. After washing, the Fabs were detected with an alkaline phospatase-coupled goat anti-human Fab antiserum diluted 1:5000 in TBST/0.5% w/v BSA.

Preparation of Natural Pollen Extracts; Identification of Group 2 Allergens by Immunoblotting Hundred mg of pollen of each grass and corn species were resuspended separately in 5 ml SDS-sample buffer and homogenized with an ultraturrax (IKA, Stauffen, Germany) for 1 min, boiled for 5 min at 95° C. and centrifuged with 14500 rpm for 5 min to remove insoluble materials. Comparable amounts of protein extracts (100 µg/slot) were then separated by a 14% SDS-PAGE under reducing conditions, stained with Coomassie Brillant Blue or blotted onto nitrocellulose (Schleicher & Schuell) (20-22).

Nitrocellulose membranes containing blotted pollen extracts from the different grass and corn species were blocked twice for 5 min and once for 30 min with TBST containing 0.5% w/v BSA at roomtemperature and then exposed overnight with bacterial extracts containing Phl p 2-specific IgE Fabs at 4° C. After washing, membranes were incubated with an alkaline phospatase-coupled goat anti-human Fab antiserum diluted 1:5000 in TBST/0.5% w/v BSA, respectively to detect bound Fabs.

Particle Blotting

Pollen grains from sweet vernal grass, oat, Bermuda grass, rye grass, timothy grass, common reed, Kentucky Bluegrass, rye, wheat, maize and birch (control) were applied to a nitrocellulose membrane in defined order using toothpicks. Membranes were placed on water-soaked Whatman paper for half an hour to allow the release of allergens. Released proteins were detected with Ponceau S (Boebringer, Mannheim, Germany) as described (19). Group 2 allergens were detected with Phl p 2-specific IgE Fabs as described for the immunoblotting. For the identification of pollen grains releasing the major birch pollen allergen Bet v 1 a recombinant mouse anti-Bet v 1 Fab was used which was detected with an alkaline phosphatase-conjugated goat anti-mouse Fab antiserum (Pierce).

IgE Competition Experiments

The ability of Phl p 2-specific IgE Fabs to inhibit the binding of grass pollen allergic patients IgE antibodies to Phl p 2 was studied by immunoblot competition experiments. Nitrocellulose strips containing equal aliquots of blotted rPhl p 2 (1 μg/cm) were blocked twice for 5 min and once for 30 min in buffer A (50 mM sodium phosphate buffer, pH 7.4, containing 0.5% w/v BSA, 0.5% v/v Tween 20 and 0.05% w/v NaN$_3$) at roomtemperature and then preincubated overnight with bacterial extracts containing Phl p 2 specific IgE Fabs and, for control purposes, with bacterial extracts containing an anti-Phl p 5 IgE Fabs (both at a concentration 5 μg/ml) at 4° C. After washing, strips were incubated overnight with sera from grass pollen allergic patients diluted 1:5 in buffer A at 4° C. Bound IgE antibodies were detected with $^{125}$I-labeled anti-human IgE antibodies (RAST, Pharmacia) and the amount of bound IgE antibodies was quantified by gamma-counting in a gamma counter (1277 Gammamaster, LKB, Wallac). All experiments were performed as duplicates with variations of less than 10% and results represent mean values. The percentage inhibition of IgE binding was calculated from the mean cpm value measured with or without addition of competing Fab. Percentage inhibition=100-cpm$_{Fab}$×100/cpm$_{control}$.

Results

The results will be discussed below in association with the accompanying sequence listing and drawings:

SEQ ID NO: 1-SEQ ID NO: 6. DNA sequence comparison of the IgE Fabs. Table 2 shows the alignment of the clone 94 heavy chain DNA sequence (SEQ ID NO: 1) with those of clones 60 (SEQ ID NO: 2) and 100 (SEQ ID NO: 3). Table 3 displays the sequence alignment of the three light chain cDNAs (clones 90 (SEQ ID NO: 4), 64 (SEQ ID NO: 5), 100 (SEQ ID NO: 6)). The Xho I and the Sac I sites are printed in italics. Framework (FR1-FR4) and hypervariable (CDR1-CDR3) regions are labeled. Identical amino acids are indicated by dashes.

SEQ ID NO: 7-SEQ ID NO: 12. Amino acid sequence alignment. Table 4 shows the alignment of the heavy chain amino acid sequences derived from three Phl p 2-specific IgE Fabs (clones 94 (SEQ ID NO: 7), 60 (SEQ ID NO: 8), 100 (SEQ ID NO: 9)) and that of the heavy chain of a homologous human IgM rheumatoid factor (accession number: Y14936). Table 5 displays the amino acid sequence alignment of the IgE Fab-derived light chains (clones 94 (SEQ ID NO: 10), 60 (SEQ ID NO: 11), 100 (SEQ ID NO: 12)) and three homologous light chains from an anti-Rh (D) antibody (AF044462) and two rheumatoid factors (S56199, S67059). The framework (FR1-FR4) and hypervariable (CDR1-CDR3) regions are labeled and identical amino acids are indicated by dashes.

BRIEF DESCRIPTION OF THE DRAWINGS

FIG. 1. Comparision of the variable heavy chain (FIG. 1A) and light chain (FIG. 1B) DNA sequence of clone 94 with the closest related germline sequences (accession numbers are printed on the left margins). The positions of the CDRs and FRs are indicated. Nucleotides are grouped in aa-encoding tripletts and identical nucleotides are displayed by dashes.

Figure 2A:
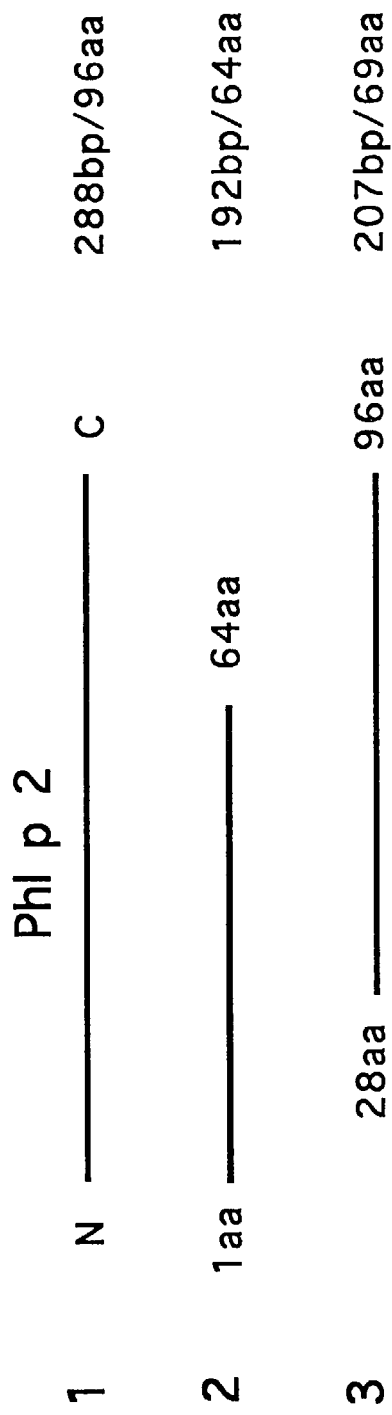
FIG. 2. Mapping of the binding site of the Phl p 2-specific human IgE Fab on the Phl p 2 allergen. Overview of the recombinant Phl p 2 fragments comprising the N-terminal 64 amino acids and the C-terminal 69 amino acids (FIG. 2A).
FIG. 2B shows a ribbon representation of the three-dimensional structure of the Phl p 2 allergen in which the N-terminal and C-terminal fragment has been indicated.
FIG. 2C: Binding of the clone 94-derived IgE Fab to nitrocellulose filters containing complete rPhl p 2 (1), the N-terminal (2), C-terminal (3) Phl p 2-derived fragments and β-gal alone (4). For control purposes, filter-bound clones were exposed to bacterial extracts from E. coli transformed with empty plasmid (pComb3H).

The Three Phl p 2-specific IgE Fabs Contain Closely Related Heavy Chain Fragments which have Recombined with Different Light Chains: Sequence Homology with Autoantibodies Framework as well as complementarity determining regions of the three heavy chain fragments (clones 94, 60, 100) were of equal size (SEQ ID NO: 1-SEQ ID NO: 3and their VH regions showed the highest similarity with members of the VH4 family (e.g., accession number: U71106; 23). The alignment of the cDNAs coding for the heavy chain variable regions of the three clones shows that they differ only in few nucleotides (27 out of 342 bp, 8% for clone 94 versus clone 60; 18 out of 342 bp, 5% for clone 94 versus clone 100; 9 out of 342 bp, 3% for clone 60 versus clone 100). The nucleotide exchanges were equally distributed over the complete variable region including frameworks and CDRs.

Sequence analysis of the light chain cDNAs revealed that they all belonged to the kappa family. The sequence comparison of the three light chains showed much greater variation than was observed among the heavy chains (SEQ ID NO: 4-SEQ ID NO: 6). Most of the nucleotide exchanges were observed in the CDRI (9%-33%) and in the CDR3 (25%-33%).

A comparison of the deduced amino acid sequences of the variable regions of the heavy chain fragments of the three rPhl p 2-specific IgE Fab clones is displayed in SEQ ID NO: 7-SEQ ID NO: 9. Clones 60 and 100 are very similar (95% sequence identity) whereas a more moderate sequence identity of 86% and 88% was observed between clones 60 ad 94, and between clones 94 and 100, respectively. The few amino acid exchanges were sometimes not conservative ones and equally distributed over the framework and complementarity determining regions of the three clones (FIG. 2A). When compared with known human variable regions a surprising sequence similarity was found to a human IgM rheumatoid factor (accession number: Y14936; 24) (FIG. 2A). With exception of the CDR3region which was completely different in sequence and length between the heavy chain fragments of the IgB Fabs and the rheumatoid factor, a comparable sequence identity was found for CDR1 and CDR2 as well as for all 4 framework regions of the IgE Fabs and the rheumatoid factor.

SEQ ID NO: 10-SEQ ID NO: 12 show the alignment of the deduced amino acid sequences of the light chains of the three clones. The amino acid sequences of the three light chains showed a considerable sequence variation, particularly in the CDR1 (27-46%) and in the CDR3 (56%). The CDR2 regions differed only in one or two aa exchanges and also in framework regions only few amino acid exchanges were noted (<10% in FRW1, <14% in FRW2, <10% in FRW3).

The three IgE Fab-derived light chains showed an interesting amino acid sequence similarity with light chains from human autoantibodies, one from a human anti-Rh (D) antibody (accession number: AF044462; 25) and two human rheumatoid factors (accession numbers S56199; S67059; 26, 27).

Figure 1A:
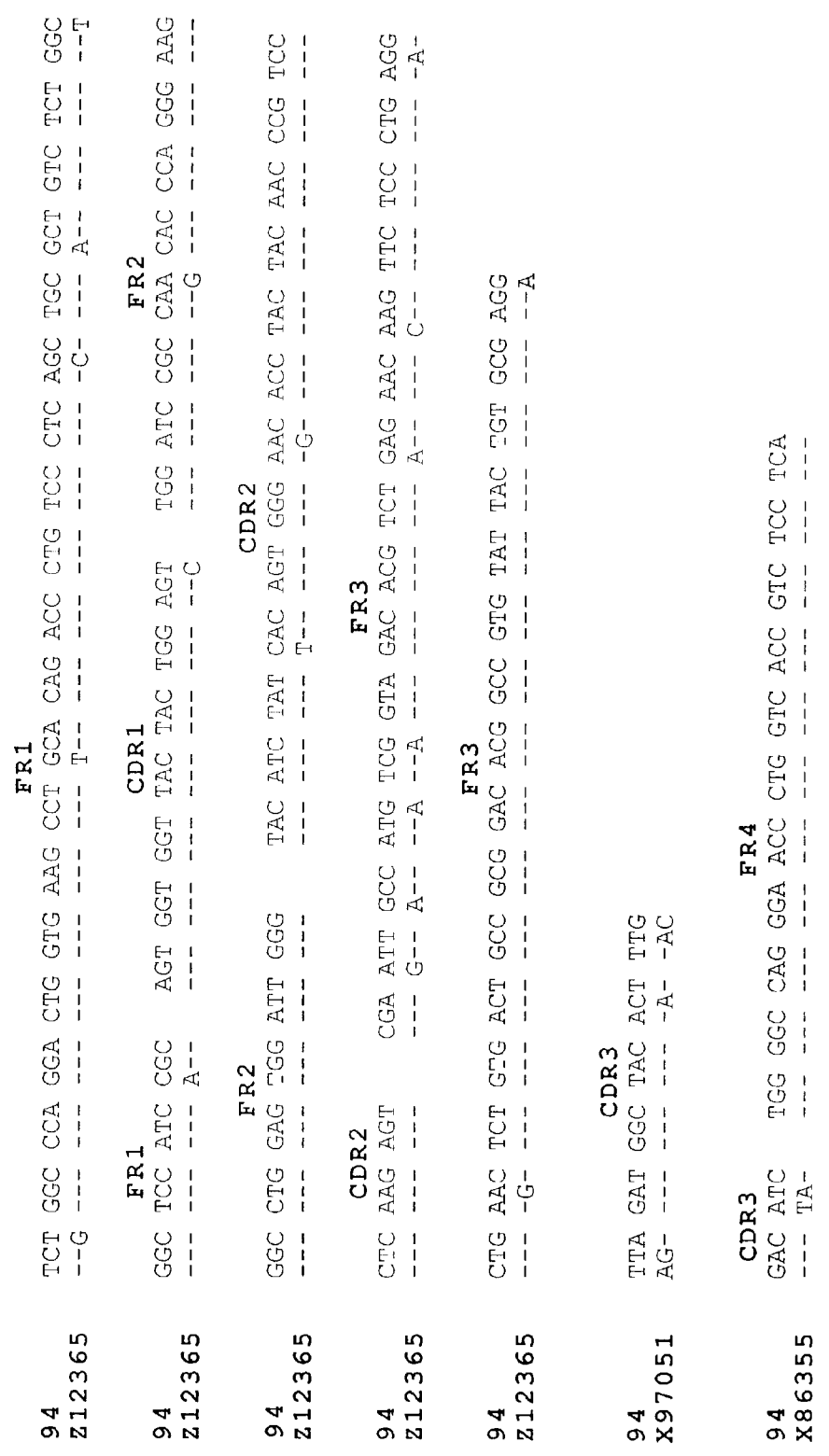

Somatic Mutations in the Variable Regions of the IgE Fabs are Indicative of an Antigen-driven Selection Process FIG. 1A shows the comparision of the DNA sequence of the variable region of the clone 94 heavy chain fragment with the closest related germlne sequences (accession number: Z12365: V-genes, FR1- FR3; X97051: D-genes, CDR3; X86355: J-genes, CDR3+FR4) (22-24). In total we found 26 nucleotide exchanges of which 11% (10/93) were found in the CDRs and 7% (16/243) were observed in the framework regions. Five of these mutations were silent whereas 18 mutations led to amino acid exchanges.

The comparision of the variable region DNA sequence of the clone 94 light chain with the most closely related germline sequences (accession number. X93627. V-genes, FR1-CDR3; J00242. CDR3+ FR4; 25, 26) is shown in FIG. 1B. We found 18 nucleotide exchanges of which 11% (9/81) were located in the CDRs and 4% (9/228) occured in the frame work regions. Most mutations were found in the CDR3.

Figure 2B:
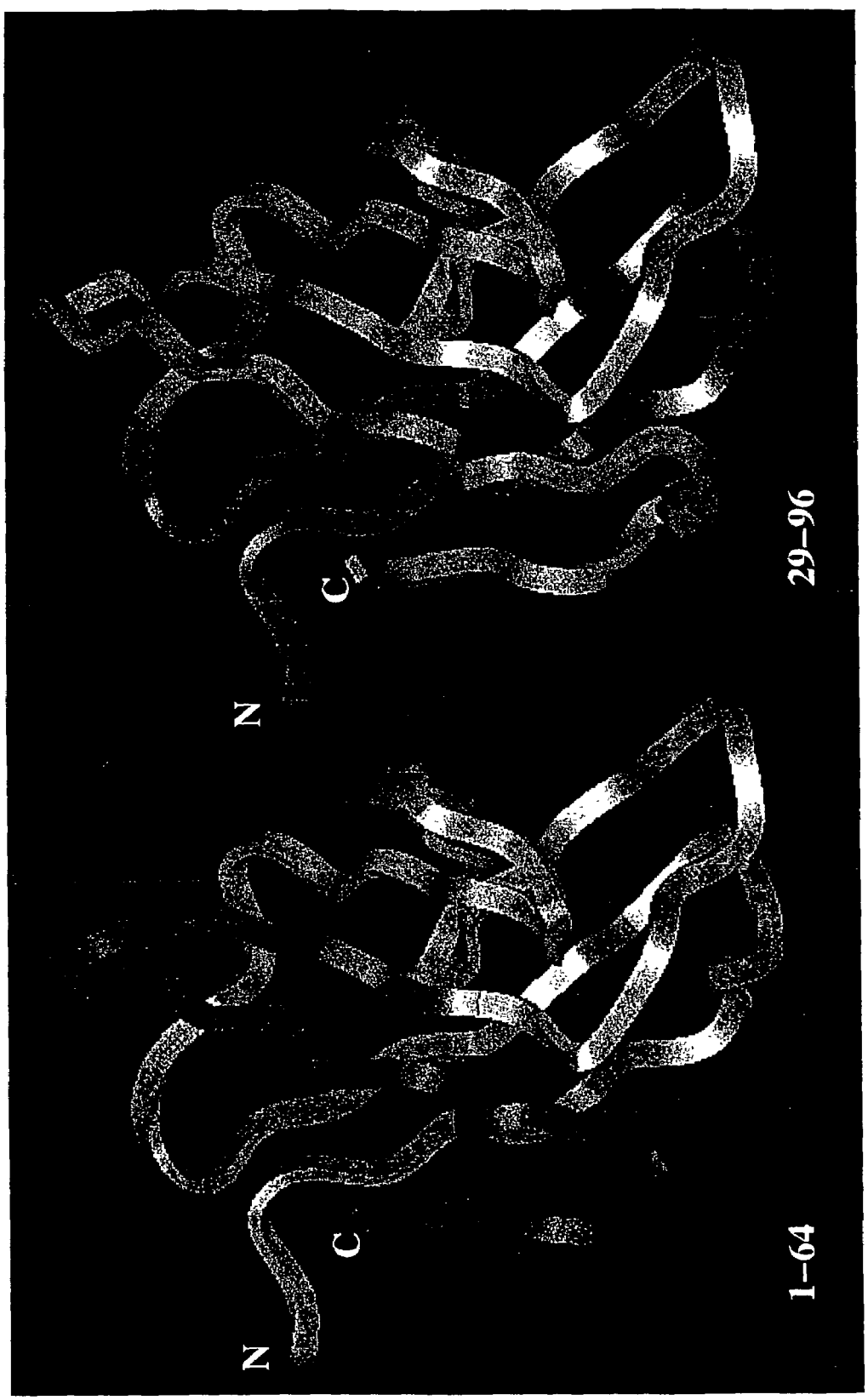
Figure 2C:
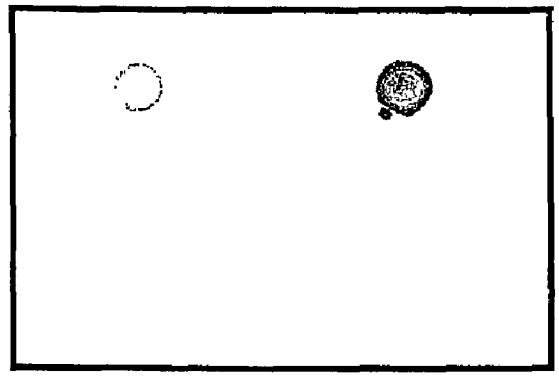
Figure 2C:
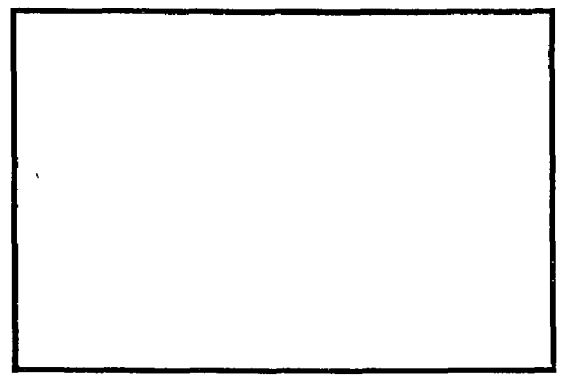
Figure 2C:
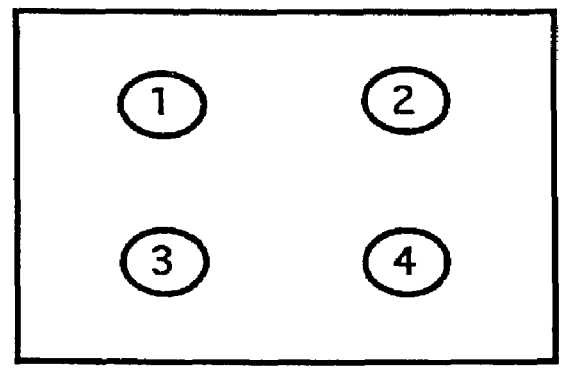

A Recombinant Fragment Comprising the N-terminal 64 Amino Acids of Phl p 2 Contains the Binding Site for the IgE Fabs In order to determine the binding site for the rPhl p 2-specific IgE Fabs, nitrocellulose-dotted complete β-gal-fused rPhl p 2 allergen (96 aa), a N-terminal rPhl p 2 fragment comprising the first 64 aa portion (1-64) and a 69 aa long C-terminal rPhl p 2 fragment (28-96 aa) were exposed to the Fabs (FIG. 2A). FIG. 2B shows a ribbon representation of the complete Phl p 2 allergen which is similar to an immunoglobulin domain and consists mainly of β-sheet structure. The N-terminal and C-terminal fragment have been indicated in the model (FIG. 2B). These two fragments were previously identified as IgE-reactive domains whereas smaller fragments did not show IgE binding capacity (8). As exemplified for clone 94, all three Phl p 2-specific IgE Fabs recognized the complete rPhl p 2 (1) and the N-terminal rPhl p 2 fragment (2) but did not bind to the C-terminal fragment (3) nor to λgt 11 phage control proteins (4) (FIG. 2C). Bacterial extracts obtained from bacteria which were transformed with the empty pComb3H plasmid did not react with any of the dotted proteins (FIG. 2C). No reactivity of the Phl p 2-specific IgE Fabs with the smaller Phl p 2 fragments described previously (8) was observed (data not shown).

Figure 3:
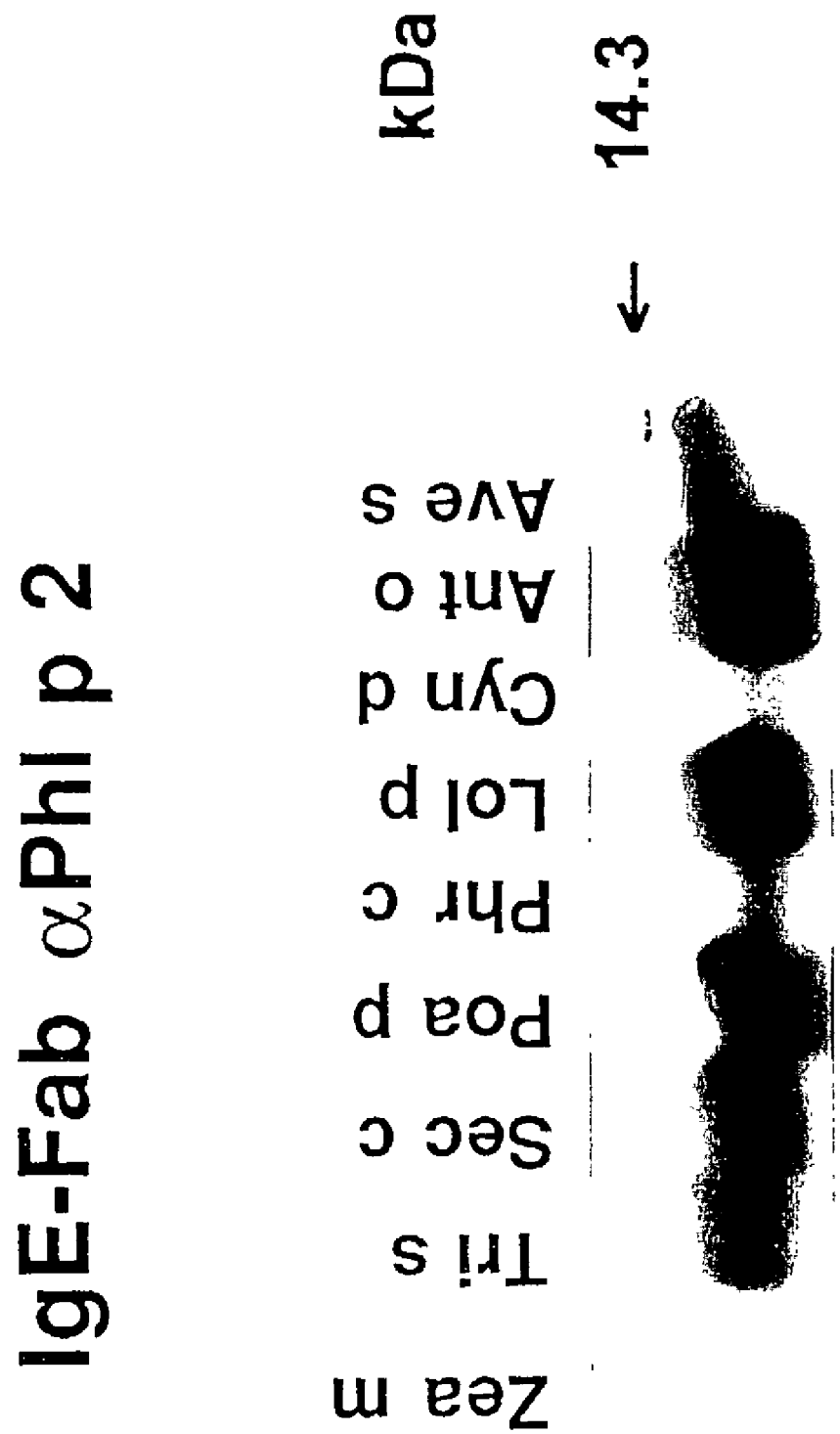
FIG. 3. rPhl p 2-specific IgE-Fabs crossreact with natural group 2 allergens from different grasses. rPhl p 2-specific IgE Fabs were tested for reactivity with nitrocellulose-blotted grass pollen extracts (Ant o: sweet vernal grass; Ave s: oat; Cyn d: Bermuda grass; Lol p: rye grass; Phr c: common reed; Poa p: Kentucky Blue grass; Sec c: rye; Tri s: wheat; Zea m: maize, Phl p: timothy grass) The position of the 14.3 kDa marker is indicated with an arrow on the right margin FIG. 4. Detection of pollen grains containing group 2 allergens by particle blotting. Pollen grains from ten different monocots (Ant o: sweet vernal grass; Ave s: oat; Cyn d: bermuda grass; Lol p. rye grass; Phl p: timothy grass; Phr c: common reed; Poa p: Kentucky Blue grass; Sec c: rye; Tri s: wheat; Zea m: maize) and birch (Bet v) were dotted to nitrocellulose. Released proteins were stained with Ponceau S (A). Group 2 allergens were detected with Phl p 2-specific IgE Fabs (B), the major birch pollen allergen, Bet v 1, with specific Fabs (C).

Anti-Phl p 2 IgE Fabs Crossreact with Natural Group 2 Allergens From 7 Grass and Corn Species and Identify Group 2 Allergen-containing Pollen by Particle Blotting In order to investigate whether the recombinant human IgE Fabs crossreacted with natural group 2 allergens from different grass and corn species, nitrocellulose-blotted natural pollen extracts from several grass and corn species were tested (FIG. 3). The IgE Fabs reacted strongly with group 2 allergens in sweet vernal grass, rye grass, Kentucky Bluegrass, rye and wheat. Only weak reactivity was observed with oat and common reed No reactivity was seen with pollen extracts from monocots reportedly lacking or containing low levels of group 2 allergens (Bermuda grass, maize) (16).

Figure 4:
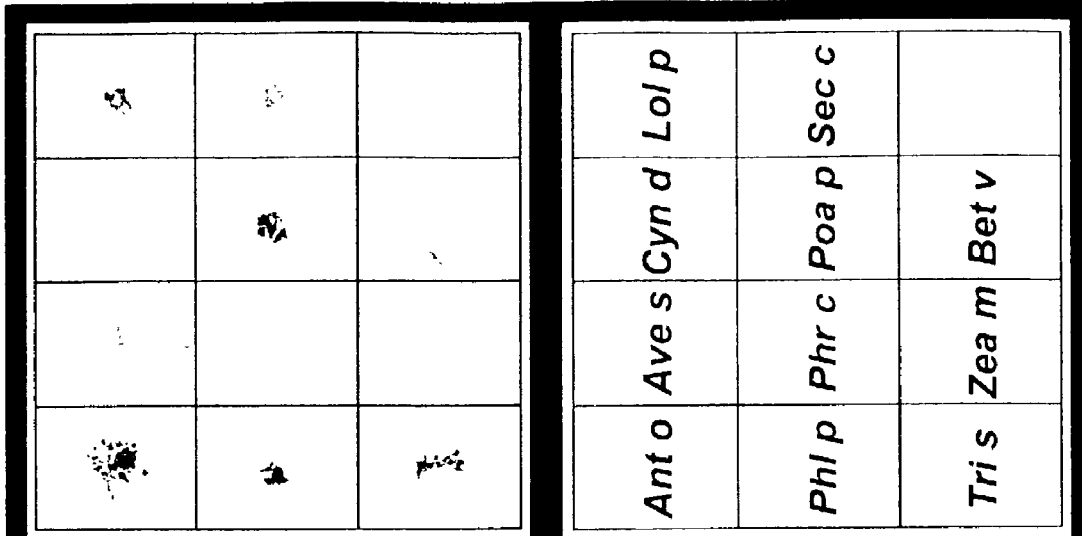
Figure 4:
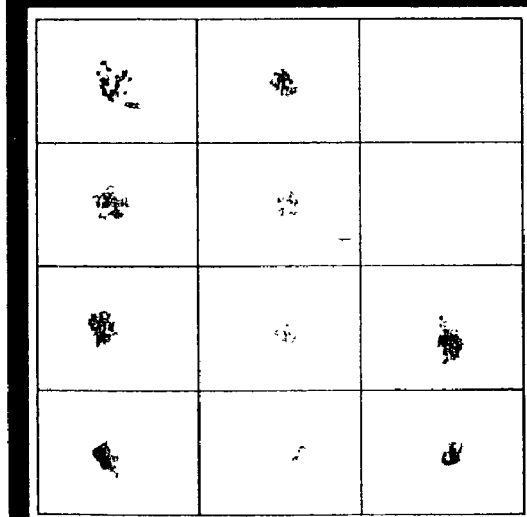
Figure 4:
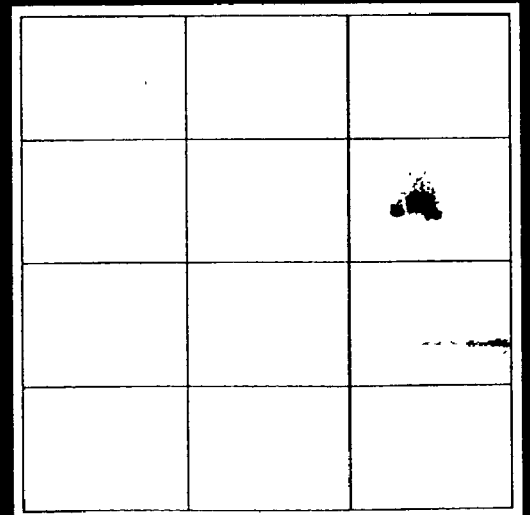

Environmental measurements of pollen allergen loads are currently performed by air sampling and analysis of pollen morphology. We demonstrate that Phl p 2-specific Fabs can be used for the immunological identification of pollen grains containing group 2 allergens by particle blotting (FIG. 4). Membran-bound pollen grains from ten different grass species and birch released proteins after hydration which were stained with Ponceau S (FIG. 4A) Phl p 2-specific Fabs identified exclusively grass pollen grains containing group 2 allergens (sweet vernal grass, rye grass, Kentucky Bluegrass, rye, wheat and oat) (FIG. 4B). A mouse Fab with specificity for the major birch pollen allergen, Bet v 1, reacted only with birch pollen confirming the specificity of the assay (FIG. 4C).

Phl p 2-specific IgE Fabs Inhibit Binding of Grass Pollen Allergic Patients IgE Antibodies to Phl p 2

Table 1 displays the quantification of IgE binding of sera from 27 grass pollen allergic patients to nitrocellulose-blotted rPhl p 2 which was preincubated with Phl p 2-specific IgE Fabs versus preincubation with Phl p 5-specific IgE Fabs (control) (Table 1) In 14 sera (52%) preincubation with Phl p 2-specific IgE Fabs reduced serum IgE binding >50% (Table 1). In 10 sera (38%) the decrease of IgE binding was between 30-50% and in the remaining 3 sera (10%) a reduction of IgE binding between 22-29% could be achieved (Table 1). An average inhibition of IgE binding to Phl p 2 in range of 52% was achieved when Phl p 2 was preincubated with Phl p 2-specific IgE Fabs (Table 1).

TABLE 1

IgE Fabs inhibit the binding of allergic patients' IgE to rPhl p 2 Sera from 27 grass pollen allergic patients (#1-27) were exposed to nitrocellulose-blotted rPhl p 2 which has been preincubated with Phl p 2-specific IgE Fabs (column A) or with control proteins (column B). The cpm values corresponding to the amount of bound IgE antibodies are displayed in columns A and B. The third column shows the percentage of inhibition of IgE binding. The mean inhibition of IgE binding is displayed at the bottom of the third column

| Patient | cpm preincubation with Phl p 2-specific Fab | | |
|---|---|---|---|
| No. | with | without | % of reduction |
| 1 | 859.2 | 1389.4 | 38 |
| 2 | 406.5 | 2570.5 | 84 |
| 3 | 93.3 | 222.7 | 58 |
| 4 | 150.7 | 228.7 | 34 |
| 5 | 734.1 | 1222.8 | 40 |
| 6 | 895.5 | 4240 | 79 |
| 7 | 6482.3 | 17914.2 | 64 |
| 8 | 130.8 | 253.1 | 48 |
| 9 | 293.5 | 523.5 | 44 |
| 10 | 1508.4 | 4274.9 | 65 |

TABLE 1-continued

IgE Fabs inhibit the binding of allergic patients' IgE to rPhl p 2 Sera from 27 grass pollen allergic patients (#1-27) were exposed to nitrocellulose-blotted rPhl p 2 which has been preincubated with Phl p 2-specific IgE Fabs (column A) or with control proteins (column B). The cpm values corresponding to the amount of bound IgE antibodies are displayed in columns A and B. The third column shows the percentage of inhibition of IgE binding. The mean inhibition of IgE binding is displayed at the bottom of the third column

| Patient No. | cpm preincubation with Phl p 2-specific Fab | | % of reduction |
|---|---|---|---|
| | with | without | |
| 11 | 2238 | 4520.1 | 50 |
| 12 | 1088.5 | 1779.7 | 38 |
| 13 | 855.9 | 1423.7 | 40 |
| 14 | 194.6 | 313 | 38 |
| 15 | 252.4 | 1014.6 | 75 |
| 16 | 312.5 | 448.4 | 30 |
| 17 | 1350.3 | 3505.3 | 61 |
| 18 | 140.4 | 387.6 | 64 |
| 19 | 1343.3 | 3485.5 | 61 |
| 20 | 129 | 416.4 | 69 |
| 21 | 704.4 | 1161.7 | 39 |
| 22 | 122.5 | 173.5 | 29 |
| 23 | 1707.4 | 2360.6 | 28 |
| 24 | 600.6 | 2036.8 | 70 |
| 25 | 3495 | 4470.6 | 22 |
| 26 | 1128.9 | 3634.8 | 69 |
| 27 | 426.4 | 1323.2 | 68 |
| | | | mean: 52 |

Discuccion

The present inventors report the molecular and immunological characterization of three human IgE antibody fragments with specificity for one of the most important environmental allergens, the major timothy grass pollen allergen, Phl p 2 The IgE Fabs were isolated from an IgE combinatorial library which was constructed from lymphocytes of a grass pollen allergic patient via panning to recombinant Phl p 2. Sequence analysis revealed that all three heavy chain fragments belonged to the VH4 family and were closely related to each other (23) While in the heavy chain variable regions the few amino acid sequence variations were equally distributed over the framework and complementarity determining regions, the kappa light chains were less closely related and showed significant sequence variations in the CDR1 and CDR3 domains We have already previously found that IgE Fabs with specificity for the major timothy grass pollen allergen consisted of identical heavy chain fragments which had recombined with different light chains (15). Furthermore it has been demonstrated that the Phl p 5-specific IgE heavy chain fragments can be recombined with light chains from antibodies with different specificity but retain antigen-specificity (15, Laffer and Valenta, unpublished data). Also our study indicates that similar heavy chain fragments can recombine with different light chains but retain specificity for the original allergen. Although we have no proof that exactly those heavy chain and light chain combinations which we isolated via the combinatorial library approach existed in the allergic patient used for construction of the library, the latter findings support the assumption that the specificity of certain IgE antibodies is dictated by the heavy chains and that promiscuous use of light chains is possible without loosing allergen specificity. In this context it is of note that all three IgE Fabs bound to the same recombinant fragment comprising the N-terminal 64 amino acids of Phl p 2.

The close sequence similarity of the heavy chain fragments as well as of the light chains of the Phl p 2-specific IgE Fabs with human autoantibodies (rheumatoid factors, anti Rh (D) antibodies) is of note in view of the fact that the recently determined three dimensional structure of Phl p 2 exhibited an unexpected similarity with immunoglobulin-like domains occuring in man (8). So far we have no evidence that the IgE Fabs can react with human proteins but when tested with pollen extracts from a variety of grass and corn species we found extensive crossreactivity with group 2 allergens. The recombinant Phl p 2-specific IgE Fabs may therefore be used to determine loads of group 2 allergens in the environment and may thus be useful for preventive measures. Furthermore they may be used for the determination and standardization of group 2 allergens in natural allergen extracts currently used for diagnosis and treatment of grass pollen allergy. Our finding that Phl p 2-specific IgE Fabs reacted with a major epitope-containing domain of Phl p 2 and strongly (mean inhibition 52%) inhibited binding of grass pollen allergic patients (n=27) complete IgE antibodies to Phl p 2 indicates a therapeutic potential of the Fabs. If the Fabs can be attached to epithelial cells or antigen-presenting cells in the target organs of atopy it may even become possible to build up a stable defense line against intruding allergens and perhaps to target them directly into the proteolytic compartment of antigen presenting cells without activating effector cells. The latter approach may not only inactivate the allergen via proteolysis but may be also useful for the induction of a protective mucosal immunity.

TABLE 2

```
                              FR1
SEQ ID NO: 1  94   CTCGAGTCTGGCCCAGGACTGGTGAAGCCTGCACAGACCCTGTCCCTCAGCTGCGCTGTCTCT
SEQ ID NO: 2  60   CTCGAG------------------------T------------------C----A--------
SEQ ID NO: 3 100   CTCGAG------------------------T------------------C----A--------

FR1                  CDR1                       FR2
SEQ ID NO: 1  94   GGCGGCTCCATCCGC  AGTGGTGGTTACTACTCGAGT   TGGATCCGCCAACACCCAGGGAAG
SEQ ID NO: 2  60   --T------------  ----------T--T-------   ---G--------G-CT---------
SEQ ID NO: 3 100   --T------------  ----------T----------   -----------G-CT---------

FR3                              CDR2
SEQ ID NO: 1  94   GGCCTGGAGTGGATTGGG  TACATCTATCACAGTGGGAACACCTACTACAACCCGTCCCTCAAG
SEQ ID NO: 2  60   ---------------C--C A----------------C-----------------------
SEQ ID NO: 3 100   ---------------C--  ------------------C-----------------------
```

TABLE 2-continued

```
                              FR3
SEQ ID NO: 1  94  AGT      CGAATTGCCATGTCGGTAGACACGTCTGAGAACAAGTTCTCCCTGAGGCTGAACTCT
SEQ ID NO: 2  60  ---      ------A-------A------------A-----C-C-----------A----C----
SEQ ID NO: 3 100  ---      ---G--A-------A------------A-----C-C----------------G----

FR3                                              CDR3
SEQ ID NO: 1  94  GTGACTGCCGCGGACACGGCCGTGTATTACTGTGCGAGG  TTAGATGGCTACACTTTGGACATC
SEQ ID NO: 2  60  -----------------------C------------C--  -C------G--T----------A-
SEQ ID NO: 3 100  ---------------------------------------  -C------G-------------A-

FR4
SEQ ID NO: 1  94  TGGGGCCAGGGAACCCTGGTCACCGTCTCCTCA
SEQ ID NO: 2  60  ---------------------------------
SEQ ID NO: 3 100  ---------------------------------
```

TABLE 3

```
                              FR1
SEQ ID NO: 4  94  GAGCTCACTCAGTCTCCATCCTCCCTGTCTGCATCTGTGGGAGACAGAGTCACCATCAGTTGC
SEQ ID NO: 5  60  GAGCTC--C---------------------C-----A--------------------C----
SEQ ID NO: 6 100  GAGCTC--G----------T---G-------------A------------------A-C---T

CDR1                                FR2
SEQ ID NO: 4  94  CGGGCAAGTCAGAGAATTAACACCTATTTAAAT  TGGTATCAGCATAAACCAGGGAAAGCCC
SEQ ID NO: 5  60  ------C-------T----G------------  -----------G-----G-----G----
SEQ ID NO: 6 100  -----G-------G-T----G--GT-GG---GCC  -----------G----------------

FR2                 CDR2                FR3
SEQ ID NO: 4  94  CTAAGCTCCTGATCTAT   GCTGCATCCAGTTTGCAAAGT   GGGGTCCCATCAAGGTTCAGT
SEQ ID NO: 5  60  ---------------GG   AG--------A----------   -----------C---------
SEQ ID NO: 6 100  ----A-----------    T--------------------   --------G-----------C

FR3
SEQ ID NO: 4  94  GGCAGTGGATATGGGACAGACTTCACTCTCACCATCAGCAGTCTGCAGCCTGAAGATTTTGCA
SEQ ID NO: 5  60  ----------C---------G-------------------A------A--------C------
SEQ ID NO: 6 100  ----------C---------T----G--------------C---------------C-----

FR3                 CDR3                    FR4
SEQ ID NO: 4  94  AGTTACTACTGT   CAAGAGAGTCTCAGTGCCTCGTACACT   TTTGGCCAGGGGACCAAGGT
SEQ ID NO: 5  60  ------------   ---C-----TA--C-A---TA--T--C   --C----CT--------AC-
SEQ ID NO: 6 100  -C------T---   ---C--GC-AA----TT-C--------   --------------------

FR4
SEQ ID NO: 4  94  GGAGATCAAACGA
SEQ ID NO: 5  60  -------------
SEQ ID NO: 6 100  ---A---------
```

TABLE 4

```
                              FR1                              CDR1
SEQ ID NO: 7  94    L E S G P G L V K P A Q T L S L S C A V S G G S I R   S G G Y Y W S
SEQ ID NO: 8  60    - - - - - - - - - - - S - - - - T - T - - - - - -   - - - - - - -
SEQ ID NO: 9 100    - - - - - - - - - - - S - - - - T - T - - - - - -   - - - - - - -
Y14936              . . . - - - - - - - S E - - - - T - - - - - Y - - S   - - . - - - G

FR2                        CDR2
SEQ ID NO: 7  94    W I R Q H P G K G L E W I G   Y I Y H S G N T Y Y N P S L K S
SEQ ID NO: 8  60    - V - - P - - - - - - - - -   N - - - - - - - - - - - - - -
SEQ ID NO: 9 100    - - - - P - - - - - - - - -   - - - - - - - - - - - - - - -
Y14936              - - - - P - - - - - - - - -   S - - - - - - - - - - - - - -

FR3
SEQ ID NO: 7  94    R I A M S V D T S E N K F S L R L N S V T A A D T A V Y Y C A R
SEQ ID NO: 8  60    - - T - - - - - - K - H - - - - T - - - - - - - - - - - - - -
SEQ ID NO: 9 100    - V T - - - - - - K - H - - - - S - - - - - - - - - - - - - -
Y14936              - V T I - - - - - K - Q - - - K - T - - - - - - - - - - - - -

CDR3                    FR4
SEQ ID NO: 7  94    L D G Y T L D I         W G Q G T L V T V S S
SEQ ID NO: 8  60    S - - - - - - N         - - - - - - - - - - -
SEQ ID NO: 9 100    S - - - - - - N         - - - - - - - - - - -
Y14936              G Y Y D I S G Y Y F D A F N I   - - - - - M - - - - -
```

TABLE 5

```
                                FR1                                      CDR1
SEQ ID NO: 10   94      E L T Q S P S S L S A S V G D R V T I S C    R A S Q R I N T Y L N
SEQ ID NO: 11   60      - - - - - - - - - - - - - - - - - - - T -    - - R - S - S - - - -
SEQ ID NO: 12  100      - - - - - - - - - V - - - - - - - - - T -    - - - - G - S S W - A
AF044462                - - - - - - A T - - L - P - E - A S L - -    - - - - S V A - - - A
S56199            E I   V - - - - - A T - - L - P - E - A S L - -    - - - - S V A - - - A
S67059                  . . . . . . . . . . . . - - - - - - T -      - - - - S - S N - - -

FR2                         CDR2              FR3
SEQ ID NO: 10   94      W Y Q H K P G K A P K L L I Y   A A S S L Q S    G V P S R F S G S G
SEQ ID NO: 11   60      - - - Q - - - - - - - - - - W   S - - N - - -    - - - - - - - - - -
SEQ ID NO: 12  100      - - - Q - - - - - - - - - - -   S - - - - - -    - - - - - - - - - -
AF044462                - - - Q - - - - - - - - - - -   - - - - - - -    - - - - - - - - - -
S56199                  - - - - - - - Q - - R - - - -   D - - N R A T    - I - - - A - - - - -
S67059                  - - - Q - - - - - - - - - - -   - - - - - - -    - - - - - - - - - -

FR3                                      CDR3
SEQ ID NO: 10   94      Y G T D F T L T I S S L Q P E D F A S Y Y C    Q E S L S A S Y T
SEQ ID NO: 11   60      S - - E - - - - - - - N - - - - - - - - - -    - Q - Y T T L - -
SEQ ID NO: 12  100      - - - - - S - - - - - - - - - - - - S - T - -    - Q A N - F P - -
AF044462                S - - - - - - - - - - - - - - - - - - T - - -    - Q - Y G T P H S
S56199                  S - - - - - - - - - - - - E - A - - - V - - -    - H R N N W P P L F T
S67059                  S - - - - - - - - - - - - - - - - - S - T - -    - Q T Y G T L I -

FR4
SEQ ID NO: 10   94      F G Q G T K V E I K R
SEQ ID NO: 11   60      - - S - - - L - - - -
SEQ ID NO: 12  100      - - - - - - - - - - -
AF044462                - - R - - - L - - - .
S56199                  - - P - - R - D V - - T V A A P S V F
S67059                  - - P - - T L D M - -
```

REFERENCES

1. Kay, A. B. (1997). *Allergy and Allergic Diseases*, Blackwell Science, Oxford, U.K.
2. Segal, D. M., Taurog, J. D., and Metzger H. (1977) Dimeric immunoglobulin E serves as a unit signal for mast cell degranulation. *Proc Natl. Acad. Sci. USA* 42, 457-467
3. Ansari, A. A., Shenbagamurthi, P., and Marsh, D. G. (1989). Complete amino acid sequence of a *Lolium perenne* (perennial rye grass) pollen allergen, Lol p II J Biol. Chem. 264, 11181-11185.
4. Ansari, A. A., Shenbagamurthi, P., and Marsh, D. G (1989). Complete primary structure of a *Lolium perenne* (perennial rye grass) pollen allergen, Lol p III: comparision with known Lol p I and Lol p II sequences. *Biochem* 28, 8665-8670.
5. Sidoli, A., Tamborini, E., Giuntini, I., Levi, S, Volonte, G., Paini, C., DeLalla, C., Siccardi, A. G., Baralle, F. E., Galliani, S, et al. (1993). Cloning, expression and immunological characterization of recombinant *Lolium perenne* allergen Lol p II J. Biol. Chem. 268, 21819-21825.
6. Dolecek, C., Vrtala, S., Laffer, S., Steinberger, P., Kraft, D, Scheiner, O, and Valenta, R. (1993). Molecular characterization of Phl p II, a major timothy grass (*Phleum pratense*) pollen allergen. *FEBS Lett* 335, 299-304
7. Roberts, A. M., Bevan, L. J., Flora, P. S., Jepson, I., and Walker, M. R. (1993). Nucleotide sequence of cDNA encoding the group II allergen of cocksfoot/orchard grass (*Dactylis glomerata*), Dac g II. *Allergy* 48, 615-623.
8. De Marino, S., Castiglione Morelli, M. A., Fraternali, F., Tamborini, E., Musco, G., Vrtala, S., Dolecek, C., Arosio, P., Valenta, R., and Pastore, A. (1999) An immunoglobuline-like fold in a major plant allergen: The solution structure of Phl p 2 from timothy grass pollen.*Structure* 7, 943-952
9. Noon, L. (1911). Prophylactic inoculation against hay fever. *Lancet* 1, 1572-1573
10. Bousquet, J., Lockey, R., Mailing, H. J., and the WHO panel members (1998). Allergen immunotherapy: Therapeutic vaccines for allergic diseases. A WHO position paper. *J. Allergy Clin. Immunol.* 102, 558-562.
11. Durham, and S. R., Till, S. J. (1998). Immunological changes associated with allergen immunotherapy. *J. Allergy Clin. Immunol.* 102, 157-164.
12. Cooke, R. A., Bernhard J. H., Hebald, S., and Stull, A. (1935). Serological evidence of immunitiy with co-existing sensitization in hay fever type of human allergy. *J. Exp. Med.* 62, 733-750
13. Loveless, M. H. (1940). Immunological studies of pollinosis: I The presence of 2 antibodies related to the same pollen-allergen in the serum of treated hay fever patients *J. Immunol.* 38, 25-50.
14. Huse, W. D., Sastry, L, Iverson, S. A. Kang, A S., Alting-Mees, M, Burton, D., Benkovic, S J., and Lerner R. A (1989). generation of a large repertoire in phage lambda. *Science* 246, 1275-1281.
15. Steinberger, P., Kraft, D, and Valenta, R. (1996). Construction of a combinatorial IgE library from an allergic patient. *J. Biol. Chem.* 271, 10967-10972.
16. Niederberger, V., Laffer, S., Froschl, R., Kraft, D., Rumpold, H., Kapiotis, S., Valenta, R., and Spitzauer, S. (1998). IgE antibodies to recombinant pollen allergens (Phl p 1, Phl p 2, Phl p 5 and Bet v 2) account for a high percentage of grass pollen-specific IgE. *J. Allergy Clin. Immunol.* 101, 258-264
17. Barbas, C. F., III, Kang, A. S., Lerner, R. A., and Benkovic, S. J. (1991). Assembly of combinatorial antibody libraries on phage surfaces: the gene III site. *Proc. Natl. Acad. Sci. USA* 88, 7978-7982
18. Sanger, F., Nicklen, S., and Coulson, A. R. (1977). DNA sequencing with chain-terminating inhibitors. *Proc.Natl. Acad. Sci. USA* 74, 5463-5467

19. Sambrook, J., Fritsch, E. F., and Maniatis, T. (1989) *Molecular cloning: A laboratory manual*, Cold Spring Harbor Laboratory Press, Cold Spring Harbor, N.Y.
20. Bradford, M. M (1976). A rapid sensitive method for quantitation of microgram quantities of protein utilizing the principle of protein-dye binding. *Anal. Biochem.* 72, 248-254
21. Fling, S. P., and Gregerson, D. S. (1986). Peptid and protein molecular weight determination by electrophoresis using a high molarity Tris buffer system without urea *Anal. Biochem.* 155, 83-88
22. Towbin, H., Staehelin, T., and Gordon, J. (1979). Electophoretic transfer of proteins from polyacrylamide gels to nitrocellulose sheets: procedure and some applications. *Proc. Natl. Acad. Sci.* 76, 4350-4354
23. Fais, F., Sellars, B., Ghiotto F., Yan, X. J., Dono, M., Allen, S. L., Budman, D., Dittmar, K., Kolitz, J., Lichtman, S., Schulman, P., Schuster, M., Vinciquerra, V., Rai, K., Stevenson, F K., Gregersen, P. K, Ferranini, M., and Chiarazzi, N. (1996).
Examples of in vivo isotype class switching in IgM+ chronic lymphocytic leukamia B cells. *J. Clin. Invest.* 98, 1659-1966
24. Williams, D. G., Mayes, S. P., and Mageed R. A. (1999) Rheumatoid factors isotype switch and somatic mutation variants within rheumatoid arthritis synovium *Immunol.* 98,123-136
25. Siegel, D. L., Chang, T. Y., Russell, S. L., and Bunya, V. Y. (1997). Isolation of cell surface-specific human monoclonal antibodies using phage display and magnetically-activated cell sorting: applications in immunohematology. *J. Immunol. Methods* 206, 73-85
26. Ermel, R. W., Kenny, T. P., Chen, P. P., and Robbins, D. L. (1993). Molecular analysis of rheumatoid factors derived from rheumatoid synovium suggests an antigen-driven response in inflammed joints. *Arthritis Rheum.* 36, 380-388
27. Martin, T., Crouzier, R., Blaison, G., Levallois, H., and Pasquali, J. L. (1993). A minor group of rheumatoid factors isolated from a patient with rheumatoid arthritis is derived from somatically mutated Vκ1 genes further evidence that rheumatoid factors during autoimmune diseases undergo an antigen driven maturation. *Autoimmun.* 15, 163-170
28. Tomlinson, I. M, Walter, G., Marks, J. D., Liewelyn, M. B., and Winter, G. (1992) The repertoire of human VH sequences reveals about fifty groups of VH segments with different hypervariable loops. *J. Mol. Biol.* 227, 776-798
29. Ravetch, J. V., Siebenlist, U., Karsmeyer, S., Waldmann, T., and Leder, P. (1981). Structure of human immunoglobulin mu locus: Characerization of embryonic and rearranged J+ D genes. *Cell* 27, 583-591
30. Mattila, P. S., Schugk, J., Wu, H., and Makela, O. (1995). Extensive allelic sequence variation in the J region of the human immunoglobulin heavy chain locus *Eur. J. Immunol.* 25, 2578-2582
31. Cox, J. P., Tomlinson, I. M., and Winter, G. (1994). A directory of human germ-line V kappa segments reveals a strong bias in their usage. *Eur. J Immunol.* 24, 827-836.
32. Hieter, P. A, Maizel, J. V. Jr., and Leder, P. (1982). Evolution of human immunoglobulin kappa J region genes. *J. Biol. Chem.* 257, 1516-1522

The invention claimed is:

1. A grass pollen group 2 allergen specific human IgE Fab having a heavy chain consisting of the amino acid sequence as shown in SEQ ID NO: 7, SEQ ID NO: 8, or SEQ ID NO: 9, and a light chain consisting of the amino acid sequence as shown in SEQ ID NO: 10, SEQ ID NO: 11, or SEQ ID NO: 12.

2. A grass pollen group 2 allergen specific human IgE Fab having a heavy chain consisting of the amino acid sequence as shown in SEQ ID NO: 7, SEQ ID NO: 8, or SEQ ID NO: 9, and a light chain consisting of the amino acid sequence as shown in SEQ ID NO: 10, SEQ ID NO: 11, or SEQ ID NO: 12, respectively.

3. An isolated grass pollen group 2 allergen specific antibody comprising the variable regions of the IgE Fab of claim 2 grafted onto human IgG1.

4. A grass pollen group 2 allergen specific human IgE Fab having a heavy chain encoded by the nucleic acid sequence as shown in SEQ ID NO: 1, SEQ ID NO: 2, or SEQ ID NO: 3, and a light chain encoded by the nucleic acid as shown in SEQ ID NO: 4, SEQ ID NO: 5, or SEQ ID NO: 6, respectively.

5. The antibody according to claim 3, wherein the antibody is directed against Phl p 2.

6. A diagnostic reagent comprising the antibody according to claim 3.

7. A diagnostic kit comprising the reagent according to claim 6.

8. The IgE Fab according to claim 2, wherein the IgE Fab is directed against Phl p 2.

9. The IgE Fab according to claim 2, wherein the IgE Fab is recombinantly produced.

10. A diagnostic reagent comprising the IgE Fab according to claim 2.

11. A diagnostic kit comprising the reagent according to claim 10.

12. A method for diagnosing type I allergy, comprising contacting a sample with the IgE Fab according to claim 2.

13. A method for environmental allergen detection, comprising contacting a sample with the IgE Fab according to claim 2.

14. A method for standardization of allergen extract, comprising standardizing the allergen extract with the IgE Fab according to claim 2.

15. A grass pollen group 2 allergen specific human IgE Fab having a heavy chain encoded by the nucleic acid sequence as shown in SEQ ID NO: 1, SEQ ID NO: 2, or SEQ ID NO: 3, and a light chain encoded by the nucleic acid as shown in SEQ ID NO: 4, SEQ ID NO: 5, or SEQ ID NO: 6.

16. An isolated grass pollen group 2 allergen specific antibody comprising the variable regions of the IgE Fab of claim 4 grafted onto human IgG1.

17. The IgE Fab according to claim 4, wherein the IgE Fab is directed against Phl p 2.

18. A diagnostic reagent comprising the IgE Fab according to claim 4.

19. A diagnostic kit comprising the reagent according to claim 18.

* * * * *